(12) United States Patent
Duvel et al.

(10) Patent No.: US 7,875,302 B2
(45) Date of Patent: *Jan. 25, 2011

(54) METHODS OF USING GRAPE SEED EXTRACT TO STIMULATE TYROSINASE GENE EXPRESSION

(75) Inventors: Lane A. Duvel, Rockford, MI (US); Diego Rua, Ada, MI (US); Stephen R. Missler, Grand Rapids, MI (US); David J. Fast, Grand Rapids, MI (US); Amitabh Chandra, Ada, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/300,095

(22) Filed: Dec. 14, 2005

(65) Prior Publication Data

US 2006/0147567 A1    Jul. 6, 2006

Related U.S. Application Data

(60) Provisional application No. 60/635,763, filed on Dec. 14, 2004.

(51) Int. Cl.
*A61K 36/87* (2006.01)
(52) U.S. Cl. .................................................. 424/766
(58) Field of Classification Search .................. None
See application file for complete search history.

(56) References Cited

U.S. PATENT DOCUMENTS

| | | | |
|---|---|---|---|
| 5,266,307 A | 11/1993 | Voorhees et al. | |
| 5,279,817 A | 1/1994 | Franco | |
| 5,916,573 A | 6/1999 | Spiers et al. | |
| 5,968,528 A * | 10/1999 | Deckner et al. | 424/401 |
| 6,126,940 A | 10/2000 | Takahashi et al. | |
| 6,235,272 B1 | 5/2001 | Greene | |
| 6,436,378 B1 | 8/2002 | Mahashabde et al. | |
| 6,482,397 B1 | 11/2002 | Scott et al. | |
| 6,551,581 B1 | 4/2003 | Mahalingam et al. | |
| 6,590,105 B2 | 7/2003 | Bradley et al. | |
| 6,620,410 B1 | 9/2003 | Cho et al. | |

FOREIGN PATENT DOCUMENTS

| | | | |
|---|---|---|---|
| EP | 1 550 667 A1 | | 7/2005 |
| FR | 2851916 A1 | * | 9/2004 |
| JP | 60100507 A | * | 6/1985 |
| JP | 03251523 A | * | 11/1991 |
| JP | 06336418 A | * | 12/1994 |
| JP | 2000159681 A2 | | 4/1999 |
| JP | 11-124318 A | | 5/1999 |
| JP | 2000-159681 A2 | | 6/2000 |
| JP | 2000159681 A | * | 6/2000 |
| JP | 2001292731 A | * | 10/2001 |
| WO | WO 2004/033475 A1 | | 4/2004 |
| WO | WO 2004/080380 A2 | | 9/2004 |

OTHER PUBLICATIONS

Tobin, D.J. and Paus, R. 'Graying: gerontobiology of the hair follicle pigmentary unit'. Exp Gerontol., vol. 36, No. 1 (2001), pp. 29-54.*
Get a beautiful tan with Grape Seed extract!, Nature Life S.A. pp. 1-2, available at: http://www.naturelife.co.za/grape_seed_extract.html (accessed Jun. 25, 2004).
Phyto, "Phyto Hair Aging Tips For Women Phytocyane", obtained at Internet address <http://hairboutique.com/tips/tips10024.htm>, on Jul. 4, 2006, dated Jan. 10, 2004, 6 pages.
International Search Report in PCT Application No. PCT/US2005/045149, dated Apr. 25, 2006, 6 pages.
Written Opinion in PCT Application No. PCT/US2005/045149, dated Apr. 25, 2006, 5 pages.
Yamakoshi, J., et al., Lightening Effect on Ultraviolet-Induced Pigmentation of Guinea Pig Skin by Oral Administration of a Proanthocyanidin-Rich Extract from Grape Seeds; Pigment Cell Res.; 16:629-638, 2003.

* cited by examiner

*Primary Examiner*—Amy L Clark
(74) *Attorney, Agent, or Firm*—Brinks Hofer Gilson & Lione; G. Peter Nichols

(57) ABSTRACT

The present invention relates to methods of increasing tyrosinase synthesis, expression, or activity in a cell comprising administering at least one grape seed extract to the cell. The grape seed extract may be obtained by any extraction process including solvent sequential fractionation and supercritical fluid extraction.

11 Claims, 3 Drawing Sheets

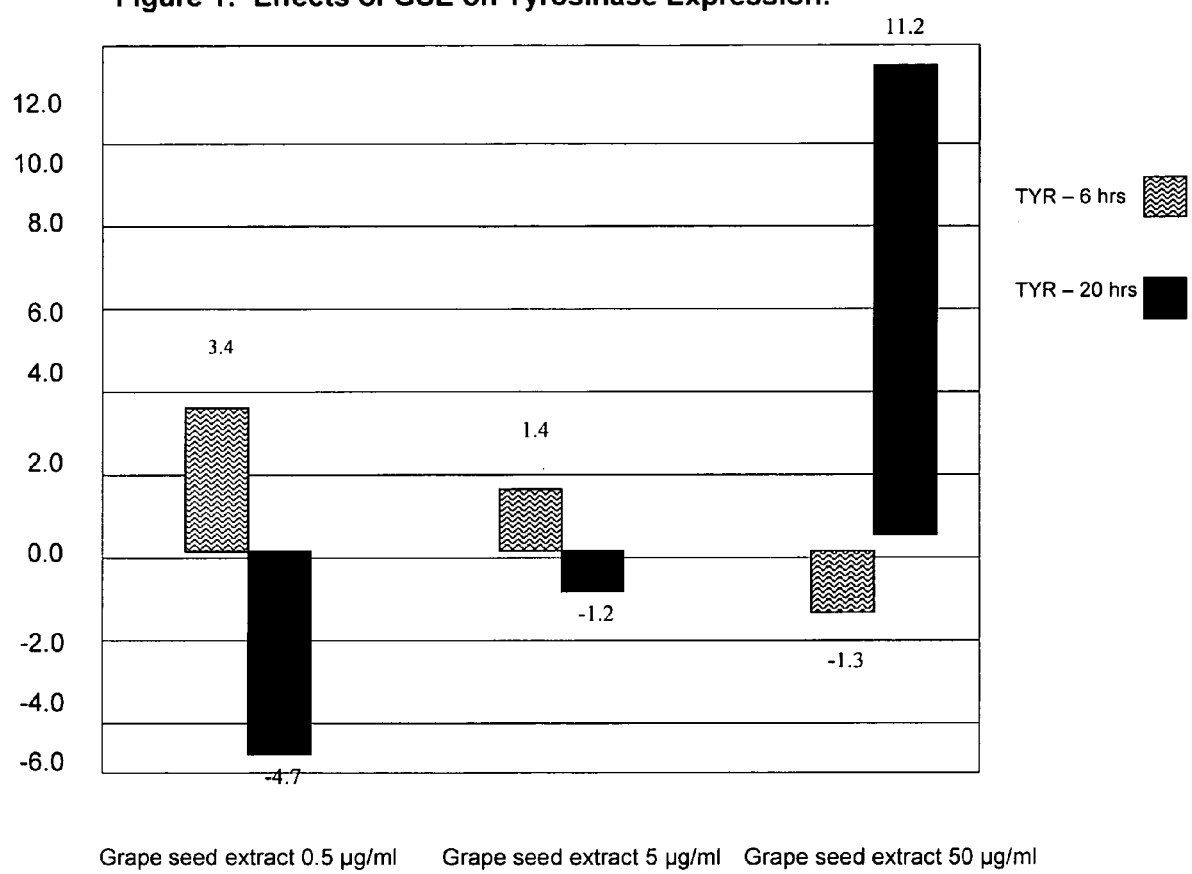
Figure 1: Effects of GSE on Tyrosinase Expression:

Figure 2: Tyrosinase Gene Expression:
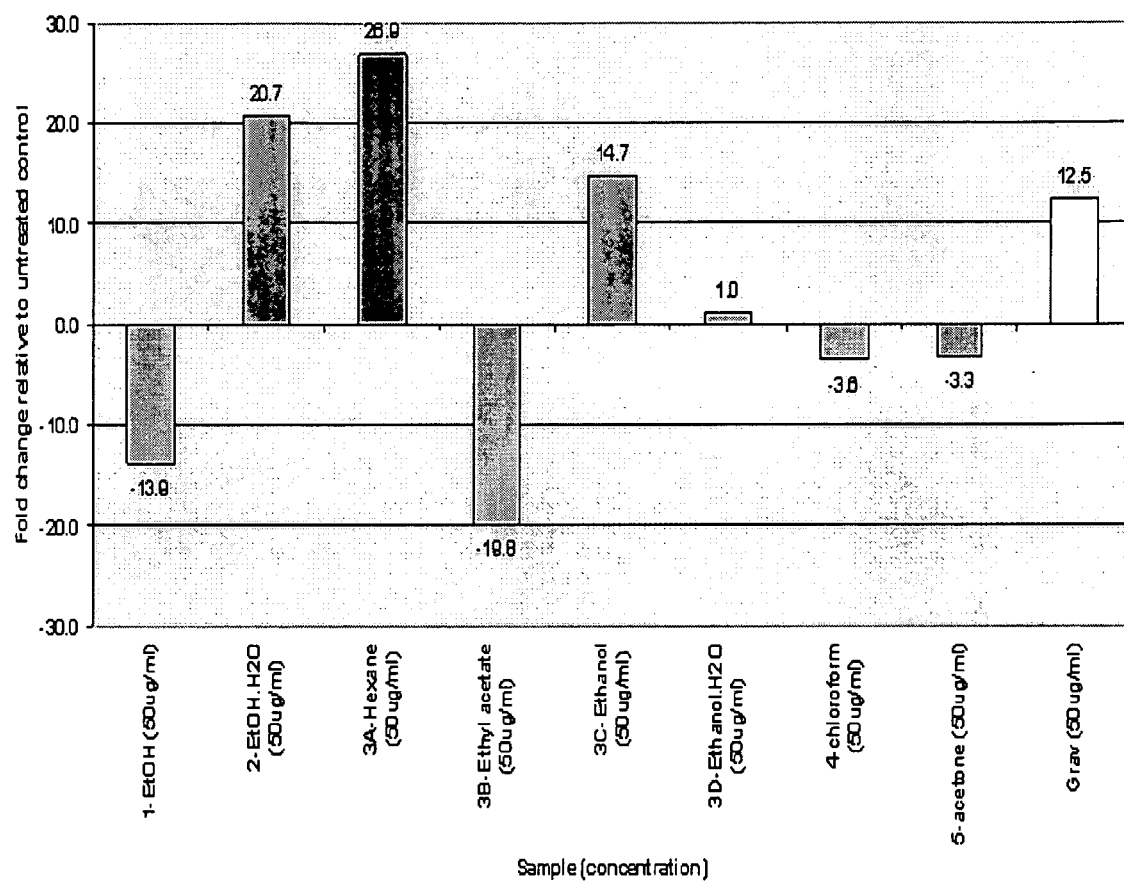

Figure 3: Tyrosinase Inhibition Activity:
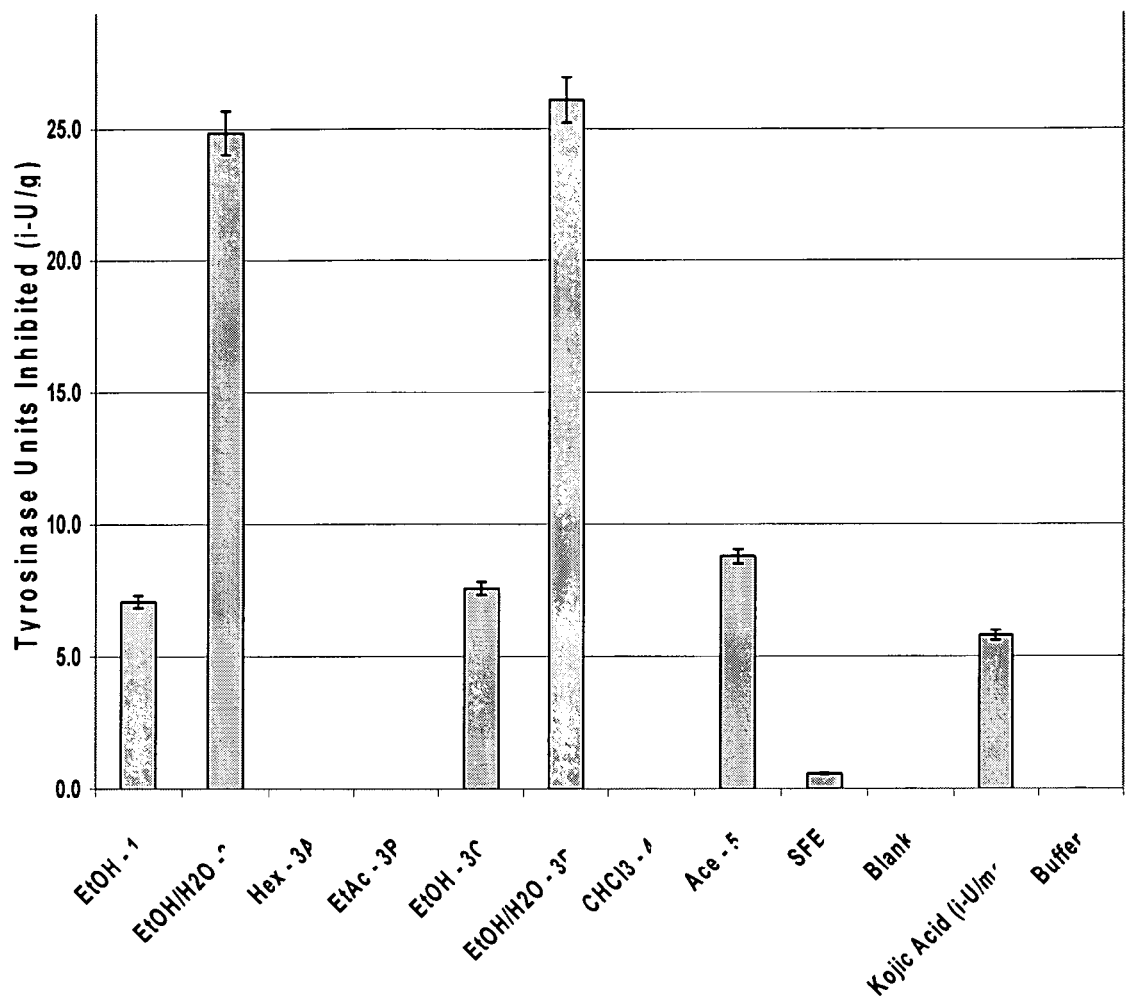

METHODS OF USING GRAPE SEED EXTRACT TO STIMULATE TYROSINASE GENE EXPRESSION

The present application claims priority to U.S. Provisional Application Ser. No. 60/635,763, filed Dec. 14, 2004.

BACKGROUND

The present invention relates to methods of stimulating tyrosinase expression or melanin synthesis in the skin or hair of a mammal comprising topically applying to the skin or hair of the mammal a composition comprising at least one grape seed extract (hereafter "GSE") and a cosmetically suitable vehicle.

A lack of gray or graying hair is generally associated with a youthful or aesthetically pleasing appearance. A sun tanned skin is also generally associated with a youthful or aesthetically pleasing appearance. However, there are disadvantages associated with current methods for covering gray or graying hair and for increasing a tanned appearance.

For example, typically, one will use a temporary or permanent hair dye to mask or cover the gray hair. These dyes, however, can be harsh, dry or damage hair, and typically fade and grow out over time, leading to dull hair and gray hair roots. Similarly, a tan appearance is typically achieved by either repeated or prolonged exposure of the skin to ultraviolet rays in sunlight or to chemical and natural stains. In recent years, prolonged exposure to ultra-violet rays, both natural and artificial, has been associated with life-threatening disorders such as melanoma or various other forms of skin cancer. Prolonged exposure to ultra-violet rays is also associated with undesirable characteristics such as wrinkled or prematurely aged skin. Chemical and natural stains for the skin may result in a non-natural skin color, may have an unpleasant odor, usually only provide a short duration of tan appearance, and are generally difficult to apply.

BRIEF SUMMARY

The various hues and degrees of pigmentation found in the skin and hair of mammals are directly related to the amount of melanin present in the skin or hair. Melanin is a pigment produced by melanocytes, which are cells found among the basal cells of the epidermis. The synthesis of melanin is catalyzed by the enzyme tyrosinase, which is expressed preferentially in melanocytes. Higher levels of tyrosinase gene expression correlate to higher levels of melanin. Higher levels of melanin in the skin and hair of a mammal correlate to darker hair and skin color.

It has been discovered that GSE, when topically applied, directly stimulates tyrosinase gene expression and results in melanin synthesis in melanocytes. Accordingly, in one embodiment, the present invention provides a method for stimulating tyrosinase gene expression or melanin synthesis in the skin of a mammal that comprises topically applying a composition comprising at least one GSE and a cosmetically suitable vehicle, to produce an increased tan appearance.

In another embodiment, the invention provides a method that includes topically applying a composition of GSE and a cosmetically suitable vehicle to the scalp of a mammal or other location where gray hair is present, to increase tyrosinase gene expression or melanin synthesis and thereby decrease gray appearance.

BRIEF DESCRIPTION OF THE DRAWINGS

FIG. 1 is a chart illustrating the regulation of the tyrosinase gene mediated by GSE in G-361 melanocyte-like cells.

FIG. 2 is a chart illustrating the effect of various GSE fractions on tyrosinase gene expression in the G-361 melanocyte-like cell line. In FIG. 2 "1-EtOH" represents an extract of a grape seed obtained using ethanol as the solvent in a total extraction procedure; "2-EtOH.H20" represents an extract of a grape seed obtained using ethanol/water as solvents in a total extraction procedure; "Hexane" represents an extract of a grape seed obtained using hexane as a solvent in a solvent sequential fractionation procedure; "Ethyl acetate" represents an extract of a grape seed obtained using ethyl acetate as a solvent in a solvent sequential fractionation procedure; "3C-Ethanol" represents an extract of a grape seed obtained using ethanol as a solvent in a solvent sequential fractionation procedure; "3D-EtOH.H2O" represents an extract of a grape seed obtained using ethanol/water as solvents in a solvent sequential fractionation procedure; "Chloroform" represents an extract of a grape seed obtained using chloroform as an extract; "Acetone" represents an extract of a grape seed obtained using acetone as an extract; and "Grav" represents a control GSE that was not subjected to any further extraction or fractionation procedures.

FIG. 3 is a chart illustrating tyrosinase inhibition activity for various GSE fractions. The data represent inhibition activity per gram of each fraction. Kojic Acid is presented as a reference, using inhibited units per milligram to accommodate the scale. In FIG. 3 "EtOH-1" represents an extract of a grape seed obtained using ethanol as the solvent in a total extraction procedure; "EtOH/H20-2" represents an extract of a grape seed obtained using ethanol/water as solvents in a total extraction procedure; "Hex-3A" represents an extract of a grape seed obtained using hexane as a solvent in a solvent sequential fractionation procedure; "EtAc-3B" represents an extract of a grape seed obtained using ethyl acetate as a solvent in a solvent sequential fractionation procedure; "EtOH-3C" represents an extract of a grape seed obtained using ethanol as a solvent in a solvent sequential fractionation procedure; "EtOH/H2O-3D" represents an extract of a grape seed obtained using ethanol/water as solvents in a solvent sequential fractionation procedure; "CHCl3-4" represents an extract of a grape seed obtained using chloroform as an extract; "Ace-5" represents an extract of a grape seed obtained using acetone as an extract; "SFE" represents an extract of a grape seed obtained using supercritical fluid extraction; "blank" represents a control; and "buffer" represents another control.

DETAILED DESCRIPTION

It is to be understood that this invention is not limited to the particular methodology or protocols described herein. It is also to be understood that the terminology used herein is for the purpose of describing particular embodiments only, and is not intended to limit the scope of the present invention which will be limited only by the claims.

Unless defined otherwise, all technical and scientific terms used herein have the same meaning as commonly understood to one of ordinary skill in the art to which this invention belongs.

The following definitions are provided in order to aid the reader in understanding the detailed description of the present invention, as well as to aid in the understanding of the appended claims.

As used herein, the singular forms "a," "an," and "the" include plural reference unless the context clearly dictates otherwise. Thus, for example, reference to "a GSE" is a reference to one or more GSEs and includes equivalents thereof known to those skilled in the art, and so forth.

"GSE" and the phrase "grape seed extract" refer to any compound or combination of compounds obtained from grape seed (i.e., polyphenols, catechins, procyanidins, flavonols, oligomeric proanthocyanidins, polymeric proanthocyanidins, gallic acid esters, etc.) and/or to any oils obtained from grape seed, as well as to chemical derivatives thereof.

The GSE used in the present invention may be obtained from commercially available sources. For example, the GSE may be obtained from Kikkoman Corporation, Polyphenolics, Inc., Bio Serae Laboratories SA, OptiPure, Dry Creek Nutrition, Inc., or other suitable sources.

Additionally, there are numerous extraction methods that can be used to produce a GSE suitable for use in the present invention. These extraction methods are described herein, well-known in the art, and may be described in various publications and patents.

"Proanthocyanidins" are flavonoids that are commonly found in GSE. Additionally, proanthocyanidins are characterized as a subset of the polyphenols which consist of the polymers of flavan-3-ols (+)-catechin, (−)-epicatechin, and (−)-epicatechin 3-O-gallate linked by C4-C8 or C4-C6 bonds. Some carry galloyl residues linked to the C-3 alcoholic function of the flavan-3-ol units.

Proanthocyanidins have well-known antioxidant properties and are procyanidolic oligomers. Typically, proanthocyanidins are known for their ability to inhibit tyrosinase. For example, see U.S. Pat. No. 6,590,105 and JP 2000-159681 by Hai Tai Confectionary Co.

"Tyrosinase" is an enzyme that plays a role in the melanin synthesis pathway and therefore its activity directly impacts the amount of melanin produced. Tyrosinase is expressed in specialized cells called melanocytes. Melanocytes encapsulate the active enzyme in subcellular organelles called melanosomes. Mature melanosomes are transferred to keratinocytes and melanin is produced. An inherited lack of tyrosinase activity results in one of the forms of albinism.

"Melanin" is a water-insoluble polymer derived from the amino acid tyrosine. It is one of two pigments found in mammalian skin and hair and adds brown/black, and red/yellow to skin and hair color pigments naturally produced by melanocytes. The degree of pigmentation is dependent on both the amount and type of melanin produced and on the physical distribution of melanosomes.

The present invention is based on the surprising discovery that topical application of at least one GSE and a cosmetically suitable vehicle directly stimulates tyrosinase gene expression and results in increased melanin synthesis. Prior to this discovery, it was generally understood that GSE contains a high level of antioxidants (proanthocyanidins), which are typically known for their ability to inhibit tyrosinase. See JP 200-159,105 and JP 2000-159681; Shi et al., "Polyphenolics in grape seeds-biochemistry and functionality." *Med Food*. 2003 Winter; 6(4):291-9.

The current state of the art concerning GSE does not recognize the unique ability of GSE to directly stimulate tyrosinase expression and thereby lead to an increased tan appearance and a decreased appearance of gray hair. Thus, the present invention provides a method that includes topically applying a composition comprising at least one GSE and a cosmetically suitable vehicle to the skin or hair of a mammal to stimulate tyrosinase expression in the vicinity of the topical application, resulting in an increased tan appearance or in a decreased appearance of gray hair.

In one embodiment, the present invention includes administration of at least one GSE at a dose ranging from approximately 30 to approximately 150 µg/ml. In another embodiment, the present invention includes administration of at least one GSE at a dose ranging from approximately 45 to approximately 75 µg/ml. In a further embodiment, the present invention includes administration of at least one GSE at a dose of approximately 50 µg/ml.

To prepare the compositions according to the present invention, at least one GSE may be mixed with a cosmetically suitable vehicle. The GSE may be present in an amount from about 0.01% to about 10% by weight of the total composition. At least one GSE may also be present in an amount from about 1% to about 9% by weight of the total composition. Alternatively, at least one GSE may be present in an amount from about 2% to about 8% by weight of the total composition. At least one GSE may also be present in an amount from about 3% to about 7% by weight of the total composition. In another alternative embodiment, at least one GSE is present in an amount from about 4% to about 6% by weigh of the total composition. In one example of a preferred embodiment of the present invention, at least one GSE is present in an amount from about 2% to about 3% by weight of the total composition.

Additionally, it is preferable that the cosmetically suitable vehicle forms from about 90% to about 99.99% by weight of the total composition, and more preferably from about 97% to 99% by weight of the total composition. The cosmetically suitable vehicle may also form from about 91% to about 98% by weight of the total composition; from about 92% to about 97% by weight of the total composition; from about 93% to about 96% by weight of the total composition; or from about 94% to about 95% by weight of the total composition. The cosmetically suitable vehicle can, in the absence of other cosmetic adjuncts or additives, form the balance of the composition.

The composition of the present invention may be formulated as a solution, gel, lotion, cream, ointment, oil-in-water emulsion, water-in-oil emulsion, stick, spray, paste, mousse, tonic, or other cosmetically suitable form.

Extracts of grape seeds from grapes of any color or variety may be used. One of ordinary skill in the art will appreciate that generally, red grape seeds have a higher total polyphenolic content than white grape seeds; 3500 mg/kg on average for reds compared to 2800 mg/kg on average for whites. See Grape Seed Extract White Paper. Prepared by: The Grape Seed Method Evaluation Committee (available at 222.activ-in.com/Testing %20White %20pater_.html). Grape seeds used in obtaining the GSE to be used in the present invention can be acquired from either grape juice operations or from wine producers after they have been discarded from the winemaking process.

Additionally, the GSE used in practicing the present invention may be obtained from any commercially available source. For example, the GSE used in practicing the present invention may be obtained from Kikkomann Corporation, Polyphenolics, Inc., Bio Serae Laboratories SA, OptiPure, Dry Creek Nutrition, Inc., or other suitable sources. Generally, grape seeds used in the manufacture of commercially available GSEs are typically derived from a variety of wine grapes, which are known to have high levels of polyphenols.

One of ordinary skill in the art will also appreciate that the GSE used in practicing the method of the present invention can be made using several extraction methods. For example, a GSE can be produced by extracting grape seed with an organic solvent. Some examples of organic solvents that might be used in producing the GSE to be used in the present invention include hexane, ethyl acetate, ethanol, and hydro-ethanol In another example, solvent sequential fractionation may be used to extract GSE. For example, using this technique, grape seeds can be sequentially extracted with hexane, ethyl acetate, ethanol, and hydro-ethanol. The extracts obtained after each step (fractions) of the sequence will contain chemical compounds in increasing order of polarity similar to the solvents used for extracting them. The fractions are dried to evaporate the solvents, resulting in GSE. Those of skill in the art will appreciate that many other solvents can be used in practicing the solvent sequential fractionation extraction of GSE.

Total hydro-ethanolic extraction techniques might also be used to obtain GSE. Generally, this is referred to as a lump-sum extraction of grape material. The extract generated in this process will contain a broad variety of phytochemicals present in the grape material including fat and water solubles. Following collection of the extract, the solvent will be evaporated, resulting in GSE.

Total ethanol extraction may also be used in the present invention. This technique also uses grape material, but ethanol, rather than hydro-ethanol, is the solvent. This extraction technique generates a GSE that may include fat soluble and/or lipophilic compounds in addition to water soluble compounds.

Another example of an extraction technique that might be used to obtain GSE is supercritical fluid carbon dioxide extraction (SFE). In this extraction procedure the grape material is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates a GSE of fat soluble and/or lipophilic compounds, similar to the total hexane and ethyl acetate extraction technique described above.

Any of the above extraction techniques, or other extraction processes and techniques in the art, may be used as part of a bio-directed fractionation process. Bio-directed fractionation focuses on determining which fraction of a GSE is responsible for the various known GSE activities. Therefore, in one example, a bio-directed fractionation technique may be used to separate polar and non-polar constituents of a GSE. In another example, GSE may be used to separate GSE constituents that increase tyrosinase synthesis and/or expression from GSE constituents that inhibit tyrosinase synthesis and/or expression.

Those of skill in the art will appreciate that there are many other extraction and fractionation processes, both known in the art and described in various patents and publications that can be used to obtain the GSE to be used in practicing the present invention. For example, the extraction procedures described in the following references, which are incorporated herein by reference, could be used in practicing the present invention: Murga et al., "Extraction of natural complex phenols and tannins from grape seeds by using supercritical mixtures of carbon dioxide and alcohol." *J. Agric Food Chem.* 2000 August;48(8):3408-12; Hong et al., "Microwave-assisted extraction of phenolic compounds from grape seed." *Nat Prod Lett.* 2001; 15(3):197-204; Ashraf-Khorassani et al., "Sequential fractionation of grape seeds into oils, polyphenols, and procyanidins via a single system employing $CO_2$-based fluids." *J. Agric Food Chem.*, 2004 May 5; 52(9): 2440-4.

The GSE to be used in practicing the present invention may be delivered topically by any means known to those of skill in the art. For example, the GSE might be delivered using a cosmetically suitable vehicle. A cosmetically suitable vehicle may act variously as solvent, carrier, diluent or dispersant for the constituents of the composition, and allows for the uniform application of the constituents to the surface of a cell or the skin at an appropriate dilution. The cosmetically suitable vehicle may also facilitate penetration of the composition into the skin, scalp, or hair follicle.

The GSE used in practicing the present invention may be soluble or insoluble in the cosmetically suitable vehicle. If the at least one GSE is soluble in the cosmetically suitable vehicle, then the vehicle acts as solvent for the GSE. However, if the at least one GSE is insoluble in the cosmetically suitable vehicle, then it is dispersed in the vehicle by means of, for example, a suspension, emulsion, gel, cream or paste, and the like.

Thus, it will be apparent to the skilled artisan that the range of possible cosmetically suitable vehicles is very broad. For example, cosmetically suitable vehicles can be emulsions, lotions, creams, or tonics. Cosmetically suitable vehicles can comprise water, ethanol, butylene glycol, or other various solvents that aid in penetration of the skin or hair follicle. Some examples of suitable vehicles are described in U.S. Pat. No. 6,184,247 and in U.S. Pat. No. 6,579,516 the entire contents of which are incorporated herein by reference.

Preferably the cosmetically suitable vehicle used in practicing the present invention comprises water and ethanol. Optionally, the cosmetically suitable vehicle also contains butylene glycol and/or frescolate MGA. For example, the cosmetically suitable vehicle can comprise 40-60% water, 45-55% ethanol, and 5-10%% butylene glycol by weight of the composition. In practicing the present invention, preferably this cosmetically suitable vehicle is mixed with at least one GSE comprising 2% by weight of the total composition. In other embodiments, the cosmetically suitable vehicle is mixed with at least one GSE comprising 0.99% to 10% by weight of the total composition; 1% to 9% by weight of the total composition; 2% to 8% by weight of the total composition; 3% to 7% by weight of the total composition; or 4% to 6% by weight of the total composition.

In general, however, cosmetically suitable vehicles according to the present invention may comprise, but are not limited to comprising, any of the following examples: water; castor oil; ethylene glycol monobutyl ether; diethylene glycol monoethyl ether; corn oil; dimethyl sulfoxide; ethylene glycol; isopropanol; soybean oil; glycerin; soluble collagen; zinc oxide; titanium oxide; Kaolin; or hyaluronic acid.

Additionally, cosmetically suitable vehicles used in the present invention may optionally comprise one or more humectants, including but not limited to: dibutyl phthalate; gelatin; glycerin; soluble collagen; sorbitol; or sodium 2-pyrrolidone-5-carboxylate. Other examples of humectants that may be used in practicing the present invention are found at page 575 of the CFTA Cosmetic Ingredient Dictionary and Handbook ($10^{th}$ ed.), and are incorporated herein by reference.

Additionally, cosmetically suitable vehicles in the present invention may optionally comprise one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; allantoin; propylene glycol; arachis oil; castor oil; isostearic acid; palmitic acid; isopropyl linoleate; lauryl lactate; myristyl lactate; decyl oleate; or myristyl myristate. Other examples of emollients that may be used in practicing the present invention are found at pages 572-575 of the CFTA Cosmetic Ingredient Dictionary and Handbook (10$^{th}$ ed.), and are incorporated herein by reference.

Additionally, cosmetically suitable vehicles used in the present invention may optionally comprise one or more penetration enhancers including but not limited to: surfactants such as pyrrolidones and alkanols, for example, 2-pyrrolidone or decanol; alcohols, such as ethanol; glycols, such as propylene glycol, dipropylene glycol, butylene glycol, ethoxydiglycol; glycerin; and terpenes.

Other cosmetically suitable vehicles that may be used in practicing the present invention will be apparent to those of skill in the art and are included within the scope of the present invention.

For example, a cosmetically suitable vehicle can be a lotion that is topically applied. In one example, the lotion may comprise cabomer 981, water, glycerin, isopropyl myristate, mineral oil, shea butter, stearic acid, glycol stearate, cetyl alcohol, dimethicone, preservatives, tea, and GSE.

The GSE compositions of the present invention may also contain various known and conventional cosmetic adjuvants so long as they do not detrimentally affect the desired melanin or tyrosinase stimulating effect provided by the at least one GSE. For example, the composition of the present invention can further include one or more additives or other optional ingredients well known in the art, which can include but are not limited to fillers (e.g., solid, semi-solid, liquid, etc.); carriers; diluents; thickening agents; gelling agents; vitamins, retinoids, and retinols (e.g., vitamin $B_3$, vitamin A, etc.); pigments; fragrances; sunscreens and sunblocks; anti-oxidants and radical scavengers; organic hydroxy acids; exfoliants; skin conditioners; moisturizers; ceramides, pseudoceramides, phospholipids, sphingolipids, cholesterol, hyaluronic acid and its derivatives, collagen synthesis promoters, glucosamine, pharmaceutically acceptable penetrating agents (e.g., n-decylmethyl sulfoxide, lecithin organogels, tyrosine, lysine, etc.); preservatives; antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, or cucumber and combinations thereof. Other suitable additives and/or adjuncts are described in U.S. Pat. No. 6,184,247, the entire contents of which are incorporated herein by reference.

Generally, the GSE composition is topically applied at least on a daily basis for a period of time sufficient to bring about the desired level of increased tan of skin or decreased gray appearance of hair. Topical application of the GSE composition may continue for any suitable period of time. More specifically, within a few days to within a few months of the initial application, a user may notice less gray hair and an increased tan appearance as well as an improvement in skin or hair texture and smoothness. It should be appreciated that the frequency with which the composition disclosed herein should be applied will vary depending on the desired level of tan appearance or the amount of gray hair to treat. In particular, the degree of cosmetic enhancement will vary directly with the total amount of composition used.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

EXAMPLES

Example 1

GSE Stimulates Tyrosinase Gene Expression in Melanocytes

According to the present invention, GSE may be used to stimulate tyrosinase synthesis and expression in melanocyte cell lines in culture. Tyrosinase is a key enzyme in the melanin synthesis pathway. Quantitative reverse transcriptase-polymerase chain reaction (qRT-PCR) can be used to measure relative levels of tyrosinase mRNA. For a description of this technique see, for example, Kawasaki et al., "Diagnosis of chronic myeloid and acute lymphocytic leukemias by detection of leukemia-specific mRNA sequences amplified in vitro." *Proc. Natl. Acad Sci USA*. 1988 August; 85(15):5698-702 and Livak et al., "Oligonucleotides with fluorescent dyes at opposite ends provide quenched probe system useful for detecting PCR product and nucleic acid hybridization." *PCR Methods Appl.* 1995 June; 4(6):357-62, which are incorporated herein by reference.

More specifically, in the present example, a mammalian melanocyte-like cell line, G-361, was treated with GSE at concentrations of 0.5, 5, and 50 µg/ml in growth media and qRT-PCR levels of tyrosinase were compared at 6 hours following treatment of G-361 with GSE and at 20 hours following treatment with GSE.

In particular, G-361 cells growing in their recommended growth media are treated with GSE dissolved in a solution containing 50% DMSO:30% Ethanol:20% Water, which allows for a final solvent (GSE) concentration not exceeding 0.5%. Additionally, G-361 cells are maintained in a growth media stock solution containing 50% DMSO:30% Ethanol:20% water to which no GSE was added, which serves as a negative control.

At six hours and twenty hours after treatment with GSE was initiated, G-361 cells from the GSE test samples and the negative control were harvested to extract total mRNA to be used as template for the quantitative RT-PCR reaction. Fold induction was calculated by comparing the level of expression of tyrosinase gene (TYR) and 18S rRNA in treated versus untreated G-361 cells.

As shown in the FIG. 1, the regulation of the tyrosinase gene mediated by GSE in G-361 melanocyte-like cells is dose dependent. The stimulatory effect became most significant at a concentration of about 50 µg/ml after 20 hours of exposure. Generally, results showing over 2-fold regulation are significant as they represent a greater than 50% change in expression. Significantly, lower concentrations of GSE, for example 0.5 µg/ml, exhibited a small inhibitory effect on tyrosinase gene expression at the 20 hour point.

Example 2

Stimulation of Melanocytes In Vitro

Melanocytes of murine origin were treated with various extracts including those of bearberry, vitamin C, and GSE at the concentration levels shown in Table 1 below. Melanocytes of murine origin were also left untreated to act as a control for melanin production and visual scoring of pigmentation.

TABLE 1

| Treatments and Concentrations | |
| --- | --- |
| Treatment Identification | Treatment Concentration |
| Control | Not applicable |
| Bearberry Extract | 2% liquid extract |
| Vitamin C | 50 µg/ml |
| GSE | 1 mg/ml |

Cells are treated with the various test extracts for approximately 96 hours. Specifically, cells are treated on day 1 and then incubated for 24 hours (day 2). Cells are again treated on day 3 and incubated for another 24 hours (day 4).

Following the 96 hour treatment period described above, melanin is extracted from the melanocytes to determine level of melanin produced following treatment. In addition, visual scoring of pigmentation is used to semi-quantitatively score pigmentation increases that occur in treated cells.

As shown below in Table 2, all three of the GSE treatments indicated an increase in melanin production based on both measured levels of melanin produced and visual scoring of pigmentation:

TABLE 2

| Induction of Melanin Production by Various Treatments | | |
| --- | --- | --- |
| Treatment Identification | % Melanin Synthesis vs. Control | Coloration: "+" sign indicates color intensity |
| None | 100 ± 11% | +++ |
| Bearberry Extract | 61 ± 5% | ++ |
| Vitamin C | 66 ± 5% | ++ |
| GSE | 143 ± 22% | ++++++ |
| GSE | 163 ± 12% | ++++ |
| GSE | 238 ± 25% | ++++ |

Example 3

Fractionation of a GSE

GSE (e.g., Gravinol-S) was subjected to bio-directed fractionation. In particular, the GSE was subjected to a total extraction, a supercritical fluid extraction, and a solvent sequential fractionation extraction, each of which are described more fully below.

More specifically, a total extraction procedure was performed using each of ethanol; ethanol and water; chloroform; and acetone as a solvent with a powdered grape seed as follows:

a) Ethanol: Powdered grape seeds (2.06 g) were extracted in ethanol (20 mL) under sonication at room temperature for 30 minutes. The sample was filtered under vacuum and supernatant was dried under nitrogen to afford 442 mg of extract/fraction.

b) Ethanol/Water: Powdered grape seeds (2.01 g) were extracted in ethanol/water, 1:1 v/v (20 mL) under sonication at room temperature for 30 minutes. The sample was filtered under vacuum and supernatant was dried under nitrogen to afford 450 mg of extract/fraction.

c) Chloroform: Powdered grape seeds (2.05 g) were extracted in chloroform (20 mL) under sonication at room temperature for 30 minutes. The sample was filtered under vacuum and supernatant was dried under nitrogen to afford 211 mg of extract/fraction.

d) Acetone: Powdered grape seeds (2.04 g) were extracted in acetone (20 mL) under sonication at room temperature for 30 minutes. The sample was filtered under vacuum and supernatant was dried under nitrogen to afford 195 mg of extract/fraction.

In addition, a GSE was obtained using a supercritical fluid extraction technique. In particular, supercritical fluid extraction was carried out using carbon dioxide as the extracting solvent under supercritical conditions. The extractions conditions were: extractor temperature 40° C., pressure 220 bars, $CO_2$ flow 20 g/minute, collector temperature 40° C., extraction time 30 minutes. Powdered grape seed sample (20 g) afforded 1.79 g of a greenish yellow oil.

A sequential fractionation technique also was used to obtain a GSE. In particular, powdered grape seeds (2.04 g) were extracted in hexane (20 mL) under sonication at room temperature for 30 minutes. The sample was filtered under vacuum and supernatant was dried under nitrogen to afford 168 mg of hexane fraction. The ability of this hexane fraction to induce melanin synthesis and tyrosinase expression was measured as described in Examples 5-7 below.

A portion of the hexane fraction was air dried and further subjected to extraction in ethyl acetate (20 mL) under sonication at room temperature for 30 minutes. The sample was filtered under vacuum and supernatant was dried under nitrogen to afford 20 mg of ethyl acetate fraction. The ability of the ethyl acetate fraction to induce melanin synthesis and tyrosinase expression was measured as described in Examples 5-7 below.

A portion of the ethyl acetate fraction was air dried and further subjected to extraction in ethanol (20 mL) under sonication at room temperature for 30 minutes. The sample was filtered under vacuum and supernatant was dried under nitrogen to afford 342 mg of ethanol fraction. The ability of the ethanol fraction to induce melanin synthesis and tyrosinase expression was measured as described in Examples 5-7 below.

A portion of the ethanol residue was air dried and further subjected to extraction in ethanol/water 1:1 v/v (20 mL) under sonication at room temperature for 30 minutes. The sample was filtered under vacuum and supernatant was dried under nitrogen to afford 184 mg of an ethanol/water fraction. The ability of the ethanol/water fraction to induce melanin synthesis and tyrosinase expression was measured as described in Examples 5-7 below.

The residue was discarded after the above step.

Example 4

Induction of Melanin Synthesis by GSE Bio-Directed Fractionation Fractions

Different GSEs were obtained using bio-directed fractionation, as described above in Example 3. In particular, the bio-directed fraction resulted in the following GSEs: an ethanol extract obtained by the above described total extraction procedure ("Ethanol-Total"); an ethanol/water extract obtained by the total extraction procedure ("Ethanol/Water-Total"); a hexane extract obtained by the sequential fractionation technique described above ("Hexane-Sequential"); an ethyl acetate extract obtained by sequential fractionation ("Ethyl Acetate-Sequential"); an ethanol extract obtained by sequential fractionation ("Ethanol-Sequential"); a chloroform extract obtained by the total extraction technique; an acetone extract obtained by the total extraction technique; an extract obtained from a supercritical fluid extraction; and a grape seed oil purchased from a grocery store. The ability of each of these extracts to induce melanin synthesis was tested.

In particular, G361 human melanoma cells were plated at $1\times10^5$/well in a 12 well plate. The cells were treated with the samples identified below in Table 3 at 50 µg/ml at 24 and 72 hours after plating. At 96 hours after plating, 1 M NaOH was added to the wells to extract cellular proteins. Extracts were boiled for 10 minutes. An aliquot of the extract was assayed for protein content using a Coomassie blue protein assay. The $OD_{450}$ of the extracts was determined. The $OD_{450}$ was normalized to the protein content of each sample and compared to that on untreated control cells. The results are reported below in Table 3:

TABLE 3

Melanin Induction Results

| Sample Description | % Control Melanin (Results normalized to viability and compared to melanin level in untreated control cells) | % Control Melanin (Results compared to melanin level in untreated control cells only) |
| --- | --- | --- |
| Ethanol-Total | 103.2 | 95.7 |
| Ethanol/Water Total | 120.8 | 72.9 |
| Hexane Sequential | 125.9 | 118.6 |
| Ethyl Acetate Sequential | 128.2 | 110.4 |
| Ethanol Sequential | 122.1 | 86.9 |
| Ethanol/Water Sequential | 116.5 | 114.2 |
| Supercritical Fluid Extraction | 119.3 | 115.9 |
| Chloroform | 123.8 | 114.9 |
| Acetone | 129.3 | 119.5 |
| Grape Seed Oil | 106.2 | 95.5 |

As shown in Table 3, the non-polar fractions (hexane, ethyl acetate, and supercritical fluid extraction) were the most potent at inducing melanin synthesis.

Example 5

Induction of Tyrosinase Gene Expression by GSE

As explained above in Example 4, GSEs induce melanin synthesis in melanocyte cell lines in culture. Therefore, the ability of each of the above-identified GSEs to induce expression of tyrosinase, a key enzyme in melanin synthesis, also was measured. In particular, relative levels of tyrosinase mRNA were determined using quantitative reverse transcriptase-polymerase chain reaction (qRT-PCR). Tyrosinase mRNA levels were measured in vitro and normalized to a housekeeping gene (18 S rRNA).

In particular, G361 human melanoma cells were treated at a dosage of 50 µg/ml with each of the following: an ethanol extract obtained by the above described total extraction procedure ("Ethanol-Total"); an ethanol/water extract obtained by the total extraction procedure ("Ethanol/Water-Total"); a hexane extract obtained by the sequential fractionation technique described above ("Hexane-Sequential"); an ethyl acetate extract obtained by sequential fractionation ("Ethyl Acetate-Sequential"); an ethanol extract obtained by sequential fractionation ("Ethanol-Sequential"); an ethanol/water extract obtained by sequential fractionation ("Ethanol/Water-Sequential"); a chloroform extract obtained by the total extraction technique; an acetone extract obtained by the total extraction technique; and a Gravinol-S non-fractionated control extract.

More specifically, the G-361 cells were treated with the various GSEs at a dosage concentration of 50 µg/ml in a stock solution growth media. The stock solution growth media was prepared in 50% DMSO:30% Ethanol:20% water to allow a final solvent concentration not exceeding 0.5% in treatment. The untreated control cells were fed a stock solution growth media of 50% DMSO:30% Ethanol: 20% water and no GSE was added.

Twenty hours after the beginning of treatment, the cells were harvested to extract mRNA to be used as a template for subsequent quantitative RT-PCR reaction. Fold induction was calculated by comparing the level of expression of tyrosinase and 18S rRNA in treated versus untreated G-361 cells. The results are reported below in Table 4 and are shown in FIG. 2.

TABLE 4

Tyrosinase Gene Induction Results

| GSE: | Fold Change Relative to Untreated Control |
| --- | --- |
| Ethanol - Total | −13.9 |
| Ethanol/Water - Total | 20.7 |
| Hexane - Sequential | 26.9 |
| Ethyl Acetate - Sequential | −19.8 |
| Ethanol - Sequential | 14.7 |
| Ethanol/Water - Sequential | 1.0 |
| Chloroform | −3.6 |
| Acetone | −3.3 |
| Gravinol-S non-fractionated control | 12.5 |

As shown above in Table 4 and in FIG. 2, tyrosinase gene induction activity was found in the ethanol-water, hexane, and ethanol fractions of a GSE. In particular, the hexane fraction showed the best induction of tyrosinase gene expression.

Example 6

Tyrosinase Inhibition Activity by GSE

GSEs are known to have an inhibitory activity on tyrosinase activity. Increased inhibition activity would be expected to reduce melanin content in a melanocyte cell culture assay. Each of the following GSEs were assayed for tyrosinase inhibition activity: an ethanol extract obtained by the above described total extraction procedure ("Ethanol-Total"); an ethanol/water extract obtained by the total extraction procedure ("Ethanol/Water-Total"); a hexane extract obtained by the sequential fractionation technique described above ("Hexane-Sequential"); an ethyl acetate extract obtained by sequential fractionation ("Ethyl Acetate-Sequential"); an ethanol extract obtained by sequential fractionation ("Ethanol-Sequential"); an ethanol/water extract obtained by sequential fractionation; a chloroform extract obtained by the total extraction technique; an acetone extract obtained by the total extraction technique; and an extract obtained from a supercritical fluid extraction.

In particular, since tyrosinase catalyzes the conversion of L-DOPA to dopachrome, in this example L-DOPA was used as a substrate and mushroom tyrosinase was used as a source of tyrosinase activity. Specifically, the conversion of colorless DOPA to dark orange dopachrome was monitored at 475 nm. The optical density of dopachrome at 475 nm is directly proportional to the intensity of orange color formation in solution (Beer-Lambert Law).

An extinction coefficient value of 3600 $M^{-1} cm^{-1}$ was used to convert absorbance units to activity. One unit of tyrosinase activity is defined as the amount required to produce one micromole of dopachrome per minute at 25° C. and pH 6.5.

The results of this analysis are reported in FIG. 3. As shown in FIG. 3, in general, extracts of nonpolar solvents (e.g. hexane, ethyl acetate, and supercritical fluid extract) yielded little inhibition activity while extracts of polar solvents (e.g. acetone, ethanol, and ethanol/water) exhibited inhibitory activity. The ethanol/water fractions showed the greatest inhibition of tyrosinase activity.

Example 7

Stimulation of Melanin Synthesis in Gray or Graying Hair

A group of test subjects having gray hair is provided with a composition of the present invention. Initially, a portion of the hair of each participant in the group will be clipped close to the lower back of the scalp and natural melanin content for each subject will be analyzed and recorded before any treatment with the composition of the present invention.

All test subjects will topically apply (to the portion of clipped hair at the back of the scalp) a standardized amount of the composition of the present invention. Such applications will occur daily for at least three months. Following at least three months of treatment, the portion of hair treated by topical application of the composition of the present invention will again be clipped and melanin content will be analyzed and recorded. An increase in melanin content indicates that the composition of the present invention is effective at stimulating melanin synthesis.

It should be understood that a wide range of changes and modifications could be made to the compositions and methods of this invention. It is therefore intended that the foregoing description illustrates rather than limits this invention, and that it is the following claims, including all equivalents, which define this invention.

The invention claimed is:

1. A method of increasing tyrosinase gene expression in skin cells, comprising administering to said skin cells a composition comprising an effective amount of a non-polar grape seed extract, wherein the non-polar grape seed extract is a hexane fraction obtained by mixing powdered grape seeds with hexane, filtering under vacuum and drying to provide the hexane fraction.

2. The method of claim 1, wherein the non-polar grape seed extract is present in an amount of about 0.01% to about 10% by weight of the composition.

3. The method of claim 1, wherein the non-polar grape seed extract is present in an amount of 1% to 9% by weight of the composition.

4. The method of claim 1, wherein the non-polar grape seed extract is present in an amount of 4% to 6% by weight of the composition.

5. The method of claim 2, wherein the non-polar grape seed extract is present in an amount of 2% to 3% by weight of the composition.

6. The method of claim 1, wherein the non-polar grape seed extract is administered in an amount ranging from approximately 30 µg/ml to approximately 150 µg/ml by weight of the total composition.

7. The method of claim 6, wherein the non-polar grape seed extract is administered in an amount ranging from approximately 45 µg/ml to approximately 75 µg/ml.

8. The method of claim 6, wherein the non-polar grape seed extract is administered in an amount of approximately 50 µg/ml.

9. The method of claim 1, wherein the skin cells are melanocytes.

10. The method of claim 1, wherein the composition further comprises a cosmetically suitable vehicle.

11. The method of claim 10, wherein the cosmetically suitable vehicle comprises water, ethanol, and butylene glycol.

* * * * *